United States Patent
Potrawa et al.

(10) Patent No.: US 7,192,471 B2
(45) Date of Patent: Mar. 20, 2007

(54) ARYL-UREIDO BENZOXAZINONE COMPOUNDS

(75) Inventors: Thomas Potrawa, Seelze (DE); Joachim Schulz, Pohle (DE)

(73) Assignee: Honeywell International Inc., Morristown, NJ (US)

( * ) Notice: Subject to any disclaimer, the term of this patent is extended or adjusted under 35 U.S.C. 154(b) by 390 days.

(21) Appl. No.: 10/949,075

(22) Filed: Sep. 24, 2004

(65) Prior Publication Data

US 2006/0065154 A1  Mar. 30, 2006

(51) Int. Cl.
- C09D 11/00 (2006.01)
- C09K 11/06 (2006.01)
- C07D 265/22 (2006.01)
- B41M 3/14 (2006.01)
- B44F 1/12 (2006.01)
- B32B 9/00 (2006.01)
- C09B 69/00 (2006.01)
- B42D 15/10 (2006.01)
- D21H 21/40 (2006.01)
- C08K 5/3437 (2006.01)

(52) U.S. Cl. .............. 106/31.15; 252/301.35; 252/301.16; 252/301.34; 544/92; 427/7; 427/8; 427/157; 428/690; 8/648; 283/92; 162/158; 162/162; 524/89

(58) Field of Classification Search .......... 106/31.15; 252/301.35, 301.16, 301.34; 544/92; 427/7, 427/8, 157; 428/690; 8/648; 283/92; 162/158, 162/162; 524/89

See application file for complete search history.

(56) References Cited

U.S. PATENT DOCUMENTS

| | | | | |
|---|---|---|---|---|
| 3,335,137 | A | * | 8/1967 | Bolotin et al. ............ 544/92 |
| 3,740,402 | A | * | 6/1973 | Cevasco ................ 544/289 |
| 3,892,972 | A | * | 7/1975 | Cevasco ............... 250/458.1 |
| 4,657,893 | A | * | 4/1987 | Krantz et al. .............. 514/18 |
| 4,673,740 | A | * | 6/1987 | Hamprecht et al. ......... 544/92 |
| 4,745,116 | A | * | 5/1988 | Krantz et al. .......... 514/230.5 |
| 5,652,237 | A | * | 7/1997 | Augelli-Szafran et al. ....... 514/230.5 |
| 5,871,854 | A | * | 2/1999 | Tokida et al. ............ 428/690 |
| 6,440,897 | B1 | * | 8/2002 | Ryu et al. ................ 503/209 |
| 6,743,283 | B2 | | 6/2004 | Imanishi et al. ........ 106/31.14 |
| 6,774,232 | B2 | * | 8/2004 | Sarkar ..................... 544/92 |
| 6,806,269 | B1 | * | 10/2004 | Kawanishi et al. ...... 514/230.5 |
| 6,951,855 | B2 | * | 10/2005 | Bird ................... 514/230.5 |
| 2004/0116420 | A1 | * | 6/2004 | Takahashi et al. ....... 514/230.5 |
| 2004/0192684 | A1 | * | 9/2004 | Ravichandran et al. .. 514/230.5 |
| 2004/0219390 | A1 | * | 11/2004 | Potrawa et al. ............ 428/690 |
| 2005/0032793 | A1 | * | 2/2005 | Abood et al. ........... 514/230.5 |
| 2005/0032795 | A1 | * | 2/2005 | Kawanishi et al. ...... 514/230.5 |

FOREIGN PATENT DOCUMENTS

EP   0 314 350 B1   10/1988

OTHER PUBLICATIONS

WIPO Publication No. WO 98/32799, dtd. Jul. 30, 1998.
WIPO Publication No. WO 02/28841, dtd. Apr. 11, 2002.
WIPO Publication No. WO 03/053980, dtd. Jul. 3, 2003.
Parfitt, Partridge and Vipond: *Cyclic Amidines. Part XVI Tetra-azanaphtho*, Journal of the Chemical Society, Abstracts, pp. 3062-3066 (1963), no month.
Von G. Doleschall and K. Lempert: *Über Wasserabspaltungsreaktion Aus N-(2-Ureidobenzoyl)-Anthranilsäuren*, Tetrachedron, vol. 24, pp. 5529-5545, no date.

* cited by examiner

*Primary Examiner*—Helene Klemanski

(57) ABSTRACT

Fluorescent pigment compounds comprising aryl-ureido benzoxazinone compounds of the general formula (I):

$$\left[ \text{benzoxazinone-aryl-ureido structure with substituents } R^1, R^3, X \right]_n \quad \text{(I)}$$

wherein $R^1$ is an substituted or unsubstituted aryl group, $R^2$ and $R^3$ are each independently selected from an H atom, an alkyl group, an alkoxy group, an alkylcarboxy group and a halogen atom, X is a carbon or sulfur atom and n is an integer of 1 or more. Many of the compounds of this class produce a yellow, generally deep yellow, emission at wavelengths of about 560 to about 585 nm when excited by an appropriate UV source. These compounds produce fluorescence making them useful as fluorescent pigments, those compounds providing emission wavelengths within the range of from about 560 to about 585 or higher when excited by a UV source are particularly useful. Those compounds having this emission spectra for the compounds makes these compounds particularly useful as pigments in security applications, particularly as pigments for use in security inks and fibers.

32 Claims, No Drawings

ARYL-UREIDO BENZOXAZINONE COMPOUNDS

FIELD OF THE INVENTION

This invention relates to new compounds that are preferably fluorescent and as such are particularly useful as fluorescent pigments in inks. More particularly, the invention relates to new aryl-ureido benzoxazinone compounds. The invention also relates to substrates containing the compounds of this invention, preferably fibers or inks containing such fluorescent pigments. A further aspect of this invention relates to processes for preparation of the new aryl-ureido benzoxazinone compounds.

BACKGROUND OF THE INVENTION

Fluorescent pigments with a Stokes Shift are well known. Especially for security applications, colorless pigments which fluoresce in the visible light area are of special interest. For security applications, especially for use as pigments in security inks, colorless fluorescent pigments that have emission wavelengths under excitation of an ultraviolet ("UV") source have been of interest. Such fluorescent pigments are known to have emission wavelengths under excitation from a UV source in the wavelength region of from about 450 nm to about 550 nm thereby providing a blue-green to green emissions. It is highly desirable to have other additional fluorescence pigments available. It is also especially desirable to have fluorescent pigments available that are able to provide emission wavelengths, under excitation of a UV source, of 560 nm or greater that are separate from the known blue-green to green emitting compounds such that further and different emission spectra pigments are available for use in security applications, such as in security inks, and are therefore able to provide a broader or greater range of security parameters. For example, compositions that emit yellow or yellow-orange are desirable.

SUMMARY OF THE INVENTION

Novel compounds of this invention are aryl-ureido benzoxazinone compounds, preferably those producing fluorescence when excited by ultraviolet light and having the general formula (I):

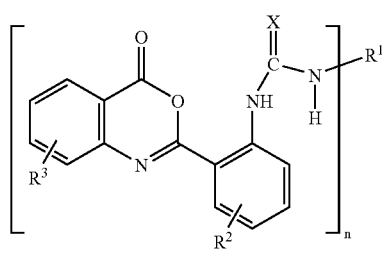

wherein $R^1$ is a substituted or unsubstituted aryl group, $R^2$ and $R^3$ are each independently selected from an H atom, an alkyl group, an alkoxy group, an alkylcarbonyl group and a halogen atom, X is an oxygen or sulfur atom, preferably an oxygen atom, and n is a positive integer of 1 or more, preferably 1 or 2, and most preferably 1 Preferably, $R^1$ is a substituted or unsubstituted phenyl, naphthyl or benzoyl group and $R^2$ and $R^3$ are each hydrogen atoms. The substituents of the substituted groups may be alkyl, alkoxy, alkylcarboxy, alkylcarbonyl, alkyl ester, cyano, halo or haloalkyl groups. Many of the compounds of this class produce a yellow, generally deep yellow, emission at wavelengths of about 560 nm to about 585 nm when excited by an appropriate UV source. Compounds providing emission wavelengths within the range of from about 560 nm to about 585 or higher when excited by a UV source are preferred and are particularly useful. One potential use of the preferred compound is as a pigment in security applications, particularly as pigments for use in security inks. Another use is as pigments in other substrates, such as in fibers, preferably polypropylene or polyamide fibers.

The ink compositions of this invention can be obtained, for example, by dissolving the fluorescent compound in an appropriate liquid medium, optionally with other ingredients employed in an ink composition. The fibers can be obtained by incorporating the pigment into the fibers during production of the fibers.

The new aryl-ureido benzoxazinone compounds of this invention are preferably prepared by reaction of anthranoylanthranilic acid with an aryl mono-, di- or poly-isocyanate or isothiocyanate to form an intermediate which undergoes ring closure by dehydration to form the compounds of this invention. Alternatively, the aryl-ureido benzoxazinone compounds of this invention may be prepared by reaction of 2-(2-aminophenyl)-4H-3,1-benzoxazinon with an appropriate aryl mono-, di- or poly-isocyanate or aryl isothiocyanate to form the compounds of this invention directly.

DETAILED DESCRIPTION OF THE PREFERRED EMBODIMENTS

The novel compounds of this invention are compounds preferably providing fluorescence upon excitation with ultraviolet light, and particularly those producing fluorescence at emission wavelengths within the range of from about 560 nm to about 585 nm or higher when excited by an appropriate UV source. The novel aryl-ureido benzoxazinone compounds of this invention have the general formula (I):

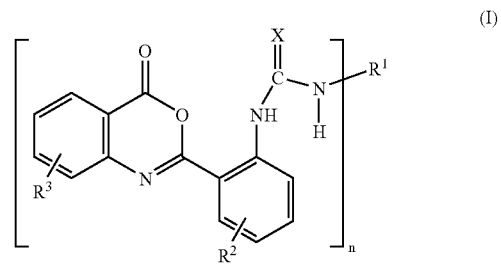

wherein $R^1$ is an substituted or unsubstituted aryl group, $R^2$ and $R^3$ are each independently selected from an H atom, an alkyl group, an alkoxy group, an alkylcarbonyl group and a halogen atom, X is an oxygen or sulfur atom, preferably an oxygen atom, and n is a positive integer of 1 or more, preferably 1 or 2, and most preferably 1. Preferably, $R^1$ is a substituted or unsubstituted phenyl, naphthyl or benzoyl group and $R^2$ and $R^3$ are each a hydrogen atom. The substituents of the substituted groups may be alkyl, alkoxy, alkylcarboxy, alkylcarbonyl, alkyl ester, cyano, halo or haloalkyl groups. Many of the compounds of this class produce a yellow, generally deep yellow, emission at wavelengths of about 560 nm to about 585 nm when excited by an appropriate UV source. The compounds of this invention produce fluorescence making them useful as fluorescent pigments, those compounds providing emission wavelengths within the range of from about 560 nm to about 585 nm or higher when excited by a UV source are particularly useful. Those compounds having this emission spectra for the compounds makes those compounds of this invention particularly useful as pigments in security applications, particularly as pigments for use in security inks.

In the compounds of formula (I) $R^1$ may be any substituted or unsubstituted aryl group, but is preferably a substituted or unsubstituted phenyl, naphthyl or benzoyl group, and is most preferably a substituted, preferably a chloro-substituted, or unsubstituted phenyl group. As examples of the substituent that may be in the substituted groups there may be mentioned the following exemplary, but non-limiting, substituents: alkyl, alkoxy, alkyl carboxy, alkylcarbonyl, cyano, halo, and haloalkyl groups. The number of carbon atoms in the alkyl or alkoxy moieties of the substituents will generally have from 1 to about 8, preferably from about 1 to about 6, and more preferably from 1 to about 4 carbon atoms. The aryl group may be substituted with one or more, preferably one or two substituent groups when it is a substituted aryl group. The aryl group, when substituted, will preferably have one or more groups selected from a methyl, a methoxy, a butyl, a fluoro, a chloro, a perfluoro, an acetoxy, a cyano or alkyl ester groups. The number of carbon atoms in the alkyl or alkoxy moieties of the $R^2$ or $R^3$ substituents will generally have from 1 to about 8, preferably from about 1 to about 6, and more preferably from 1 to about 4 carbon atoms. Preferably, $R^2$ and $R^3$ are each a hydrogen atom. Preferred compounds are those wherein $R^2$ and $R^3$ are each a hydrogen atom, $R^1$ is phenyl or para-chloro phenyl, X is oxygen and n is 1.

The preferred aryl-ureido benzoxazinone compounds of the general formula (I) of this invention may be prepared such as by a reflux reaction of anthranoylanthranilic acid with an aryl mono-, di- or poly-isocyanate or isothiocyanate in a suitable reaction solvent, such as methylethylketone and a ring closure rearrangement of the resulting intermediate through use of a suitable dehydration agent, such as diacetic anhydride, to form the compounds of formula (I). Such a reaction is illustrated by the following Reaction Method (A). This is a preferred method of synthesis since anthranoylanthranylic acid is a readily available, relatively inexpensive reactant. Alternatively, the compounds of formula (I) may be prepared by a reflux reaction of 2-(2-aminophenyl)-4H-3,1-benzoxazinon with an aryl mono-, di- or poly isocyanate or isothiocyanate in a suitable reaction solvent, such as methylethylketone. Such a reaction is illustrated by the following Reaction Method (B). In both Reaction Methods (A) and (B), $R^1$, $R^2$, $R^3$ and n are as defined for formula (I).

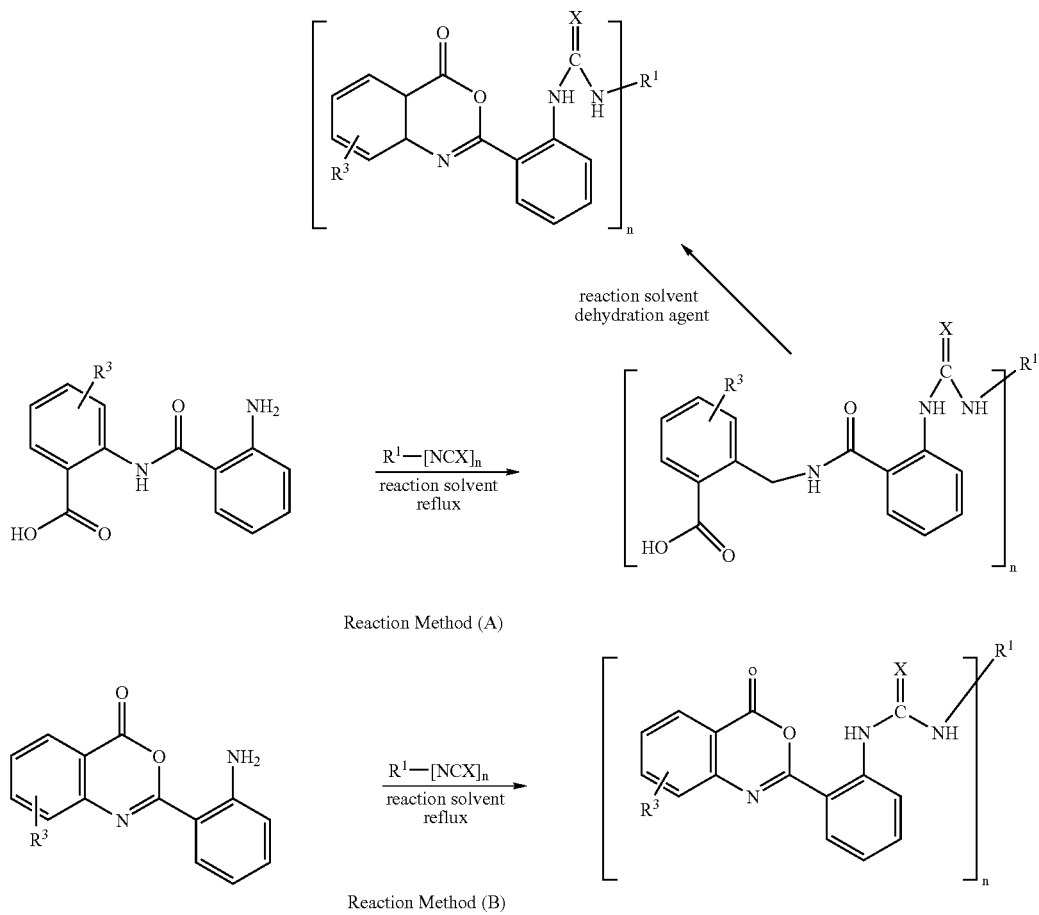

Reaction Method (A)

Reaction Method (B)

Preferably, when the compounds of formula (I) of this invention are excited by an ultraviolet light source, they exhibit emission wavelengths providing fluorescence making them useful as pigment in security application, such as for example, as pigments in security inks and fibers. While the range of emissions wavelengths for the compounds of formula (I) vary from about 400 nm to about 585 nm, the most preferred compounds exhibit emission wavelengths in the range of from about 560 nm to about 585 nm. These latter compounds thus provide a yellow color, and particularly a deep yellow color. In addition, the compounds of this invention show fastness which is excellent enough to use as an ultraviolet type excitation fluorescent developer for ink compositions. Compounds providing emission wavelengths within the range of from about 560 nm to about 585 nm or higher when excited by a UV source are particularly useful. Those compounds having this emission spectra for the compounds makes those compounds of this invention particularly useful as pigments in security applications, particularly as pigments for use in security inks and fibers. For example, the ink compositions of this invention may be employed on a variety of indicia or data carrier substrates, including but not limited to, uses such as on or in currency, passports, chip cards, checks, check cards, credit cards, debit cards, identity cards, certificates, and bank notes and the like.

Preferably, ink compositions of the present invention can be obtained by dissolving a compound of this invention of formula (I) in a suitable liquid medium, generally any organic solvent, such as, but not limited to an aliphatic alcohol, ester or ketone solvent, and optionally mixing therewith one or more ingredients usually contained in ink compositions, such as for example, binder resins, surfactants and the like. The compound of this invention is dissolved in the ink composition in any suitable amount, generally in an amount of from about 0.001% to about 15%, preferably from about 0.01% to about 3% by weight based on the total weight of the ink composition. Preferably, the amount should provide an acceptable amount of light emission sufficient to determine or read the emission, either by the human eye or a detector capable of sensing such fluorescence). However, amounts so great as to cause self-absorption causing emission intensity to be reduced are preferably avoided. Typical examples for the preparation of ink compositions are disclosed in U.S. Pat. No. 6,743,283 B2, the disclosure of which is incorporated herein by reference thereto.

The solvent that is employed for dissolving the compounds of this invention in ink compositions may be any suitable organic solvent, but will preferably be an aliphatic alcohol solvent where adverse environmental effects or odor can be avoided or minimized. If in such circumstances, the compounds of this invention are not sufficiently soluble in just the aliphatic alcohol, a mixture of the alcohol and another solvent, such as an organic ester, e.g., ethyl acetate, or a ketone, e.g., methylethylketone, methylisobutylketone and the like, will generally be employed.

Where it is important that the ink composition have increased stability or for preventing the ink from drying out prematurely, the ink compositions of this invention may include a high boiling point solvent, such as for example, an ether solvent like ethylene glycol monomethyl ether, ethylene glycol monoethyl ether, propylene glycol monomethylether, or aliphatic polyols such as 1,2-hexanediol, 2,4,6-hexanetriol and the like.

In the luminous ink composition of the preferred present invention, a binder resin is often included in order to fix the inventive compound properly. It is preferred that the binder resin has good solubility to the solvent, and that viscosity of the ink composition is suitably adjusted when the binder resin is included in the ink composition. Specific examples of the preferred binder resins include the resins listed below: a polyvinyl resin such as polyvinyl alcohol, polyvinyl butyral, polyvinyl pyrrolidone, vinyl pyrrolidone-vinyl acetate copolymers; a polyamine resin such as polyallylamine, polyvinylamine and polyethyleneimine; a polyacrylate resin such as polymethyl acrylate, polyethylene acrylate, polymethyl methacrylate and polyvinyl methacrylate; and an amino resin, an alkyd resin, an epoxy resin, a phenol resin, a polyesterimide resin, a polyamide resin, a polyamideimide resin, a silicone resin, a phenol resin, a ketone resin, rosin, a rosin-modified resin phenol, maleic acid, fumaric acid resin, and the like), a petroleum resin, a cellulose resin such as ethyl cellulose and nitrocellulose, and a natural resin (gum arabic, gelatin, and the like.)

Particularly preferred binder resins include a polyvinyl resin, a polyacrylate resin, a polyamine resin, etc., which are usually employed for ink for writing implements, ink jet ink, and printing ink.

These binder resins are blended, for example, in an amount of from about 0.5% to 30% by weight, preferably from about 1% to about 20% by weight based on the total weight of the ink composition. If the amount of the binder resin is too low, typically less than about 0.5% by weight, the luminous compound may not satisfactorily be fixed on impermeable recording materials. On the other hand, if the amount is too high, typically over about 30% by weight, the resulting ink composition may become poor in injection stability. Further, a binder layer may cover thickly around a luminous compound, emission of the luminous compound may be impaired by the binder resin.

The ink composition of this invention, when desired or needed may include some additives such as various types of surfactants, e.g., an anionic, nonionic and cationic surfactants such as alkylsulfate, phosphate and polyoxyethylene alkyl ether and alkylamine salt; ampholytic surfactants, fluorine-containing surfactants, or acetylene glycol surfactants, a dispersant e.g., rosin acid soap, stearic acid soap, oleic acid soap, Na-di-.beta.-naphthylmethane disulfate, Na-lauryl sulfate and Na-diethylhexyl sulfosuccinate), or cyclodextrin (CD) beta-CD, dimethyl-beta-CD, methyl-beta-CD, hydroxyethyl-beta-CD and hydroxypropyl-beta-CD, and antifoaming agents and the like. These additives may be employed in an amount of from about 0.5% to about 5% by weight, preferably from about 1% to 3% by weight based on the total weight of the ink composition.

The methods for the preparation of the compounds of formula (I) of this invention are illustrated by the following two examples.

EXAMPLE 1

1-Phenyl-3-[2-(4-oxo-4H-benzo[d][1,3]oxazin-2-yl)-phenyl]-urea by Reaction Method (A)

A 250 ml three-neck bottle was charged under room temperature with 12.8 g [0.05 mol] anthranoylanthranilic acid and 100 ml methylethylketone. Under stirring 5.95 g [0.05 mol] phenylisocyanate was added and heated for about 4 hours under reflux about 80° C.). After this the suspension was cooled down to about. 40° C. Then 40 ml acetanhydrid was added and then heated additionally for 3 hours. After cooling down to 10° C. the precipitate was sucked off, washed with acetone and dried at 50° C. under normal pressure.

Yield: 12.5 g (70%) of an off-white powder which shows under excitation with long UV light (366 nm) a yellow-orange fluorescence (Flu-Max at 567 nm).

With Differential Thermoanalysis (DTA) there was shown one endothermic peak (melting) at 235° C.

EXAMPLE 2

1-Phenyl-3-[2-(4-oxo-4H-benzo[d][1,3]oxazin-2-yl)-phenyl]-urea by Reaction Method (B)

A 250 ml three-neck bottle was charged under room temperature with 11.3 g [0.05 mol] 2-(2-Aminophenyl)-4H-3,1-benzoxazinon and 100 ml methylethylketone. Under stirring 5.95 g [0.05 mol] phenylisocyanate was added and heated for about 30 min under reflux (about. 80° C.). After this the suspension is cooled down to about 10° C., the precipitate was sucked off, washed with 50 ml acetone and dried at 50° C. under normal pressure. The properties are the same as from the product manufactured by Method A in Example 1.

According to above described methods, different aryl-benzoxazinone-phenyl-urea compounds of formula (I) of this invention were synthesized by employing the appropriate aryl mono-, di- or poly-isocyanate or thioisocyanate reactant. The yields are between about 60% and about 90%, depending on the aryl-isocyanate or isothiocyanate reactant employed in the reaction. The fluorescence maxima for the compounds are generally between 540 nm and 585 nm. The compounds so prepared are illustrated in the following table of compounds. In the Table headings "Excmax" is the excitation wavelength in nm for the compounds, "Flumax" is the fluorescence wavelength in nm for the compounds, "X" and "Y" represent the color location on the standard color chart (DIN 5033), and "DTA" is Differential Thermoanalysis melting point in ° C. Excitation and emission maxima of the compounds were measured with a Shimadzu RF-5000 fluorescence spectrophotometer. Brightness of the fluorescence under excitation with 366 nm light were measured with a Minolta luminancemeter LS-11 and given as intensities in $cd/m^2$

TABLE

| Structure | Cmpd. No. | Excmax [nm] | Flumax [nm] | X | Y | UV brightness [cd/m$^2$] | DTA Peak |
|---|---|---|---|---|---|---|---|
| (structure 1) | 1 | 385 | 567 | 0.486 | 0.496 | 65 | 235° |
| (structure 2) | 2 | 350–375 | 585 | 0.439 | 0.3 | 8 | 241° |
| (structure 3) | 3 | 360–400 | 565 | 0.483 | 0.501 | 100 | 213° |
| (structure 4) | 4 | 395 | 560 | 0.456 | 0.516 | 136 | 217° |

TABLE-continued

| Cmpd. No. | Structure | Excmax [nm] | Flumax [nm] | X | Y | UV brightness [cd/m²] | DTA Peak |
|---|---|---|---|---|---|---|---|
| 5 | (2-methylphenyl urea derivative) | 365 | 565 | 0.465 | 0.498 | 71 | 240° |
| 6 | (4-methylphenyl urea derivative) | 385 | 575 | 0.492 | 0.472 | 14 | 233° |
| 7 | (2,3-dimethylphenyl urea derivative) | 360–400 | 560 | 0.457 | 0.51 | 96 | 243° |
| 8 | (2,6-dimethylphenyl urea derivative) | 375 | 565 | 0.472 | 0.503 | 70 | 250° |

TABLE-continued

| Cmpd. No. | Structure | Excmax [nm] | Flumax [nm] | X | Y | UV brightness [cd/m²] | DTA Peak |
|---|---|---|---|---|---|---|---|
| 9 | (4-propyl-phenyl urea derivative) | 350 | 575 | 0.49 | 0.462 | 16 | 233° |
| 10 | (3-trifluoromethyl-phenyl urea derivative) | 375 | 540 | 0.387 | 0.578 | 274 | 234° |
| 11 | (3-fluoro-phenyl urea derivative) | 375 | 560 | 0.465 | 0.512 | 100 | 234° |
| 12 | (3-chloro-phenyl urea derivative) | 370 | 560 | 0.46 | 0.522 | 135 | 232° |

TABLE-continued

| Cmpd. No. | Structure | Excmax [nm] | Flumax [nm] | X | Y | UV brightness [cd/m²] | DTA Peak |
|---|---|---|---|---|---|---|---|
| 13 | 4-chlorophenyl urea linked to 2-phenyl-4H-benzo[d][1,3]oxazin-4-one | 375 | 560 | 0.462 | 0.522 | 150 | 254° |
| 14 | 2-chlorophenyl urea linked to 2-phenyl-4H-benzo[d][1,3]oxazin-4-one | 375 | 560 | 0.45 | 0.521 | 120 | 246° |
| 15 | 3,4-dimethoxyphenyl urea linked to 2-phenyl-4H-benzo[d][1,3]oxazin-4-one | | | | | | 221° |
| 16 | 3-methoxyphenyl urea linked to 2-phenyl-4H-benzo[d][1,3]oxazin-4-one | 380 | 560 | 0.467 | 0.518 | 84 | 222° |

TABLE-continued

| Cmpd. No. | Structure | Excmax [nm] | Flumax [nm] | X | Y | UV brightness [cd/m²] | DTA Peak |
|---|---|---|---|---|---|---|---|
| 17 | 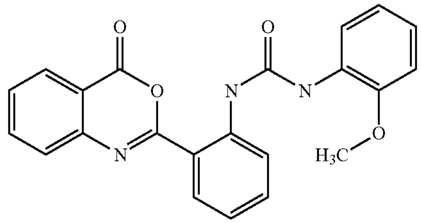 | 350–400 | 450,575 | 0.378 | 0.346 | 18 | 240° |
| 18 | 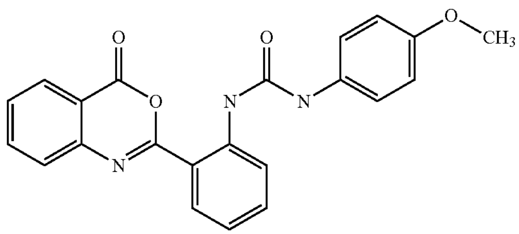 | | | | | 0.3 | 234° |
| 19 | 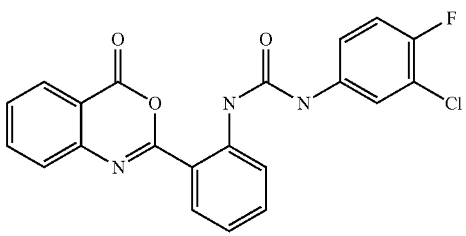 | 382 | 548 | 0.377 | 0.487 | 150 | |
| 20 | | | | | | | |
| 21 | 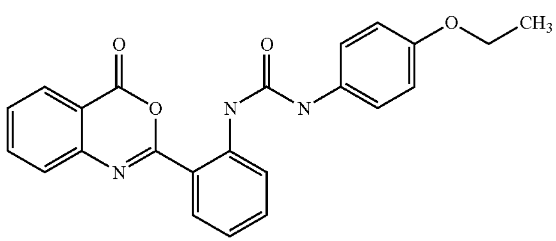 | 289–294 | 468 | 0.282 | 0.295 | 0.4 | |

TABLE-continued
| Structure | Cmpd. No. | Excmax [nm] | Flumax [nm] | X | Y | UV brightness [cd/m²] | DTA Peak |
|---|---|---|---|---|---|---|---|
| 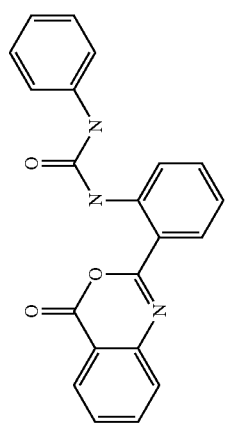 | 22 | 381 | 433 | 0.231 | 0.251 | 84 | |
| 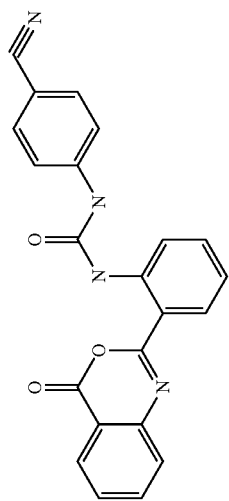 | 23 | 381 | 533 | 0.359 | 0.6 | 380 | |
| 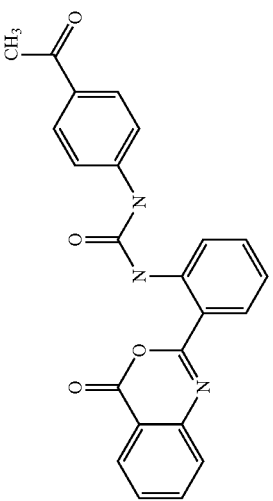 | 24 | 382 | 546 | 0.421 | 0.56 | 195 | |

TABLE-continued

| Cmpd. No. | Structure | Excmax [nm] | Flumax [nm] | X | Y | UV brightness [cd/m²] | DTA Peak |
|---|---|---|---|---|---|---|---|
| 25 | 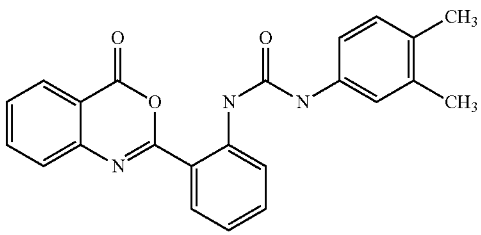 | 362 | 572 | 0.448 | 0.478 | 25 | |
| 26 | 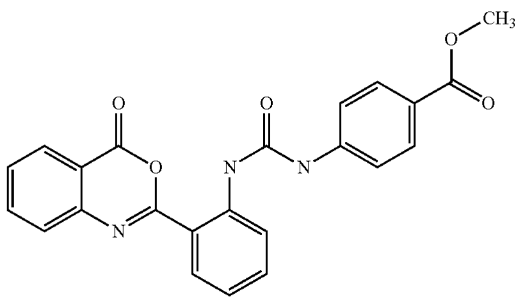 | 381 | 560 | 0.468 | 0.52 | 150 | |
| 27 | 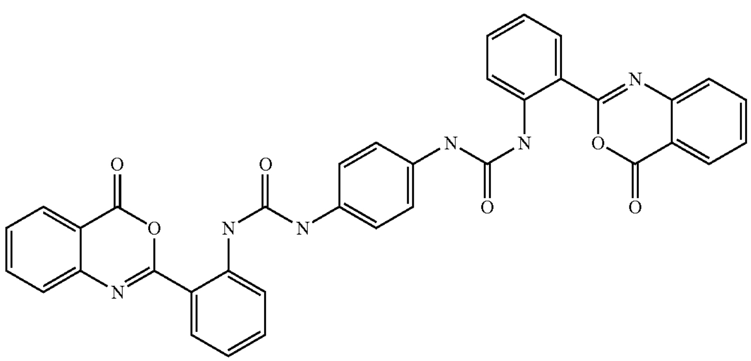 | 385 | 443 | 0.214 | 0.239 | 65 | |

TABLE-continued

| Cmpd. No. | Structure | Excmax [nm] | Flumax [nm] | X | Y | UV brightness [cd/m²] | DTA Peak |
|---|---|---|---|---|---|---|---|
| 28 | 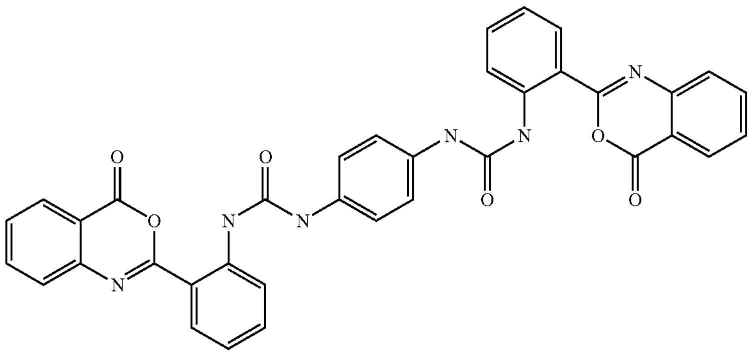 | 383 | 418 | 0.256 | 0.282 | 39 | Modification (ex mother liquer of previous compound) |
| 29 | 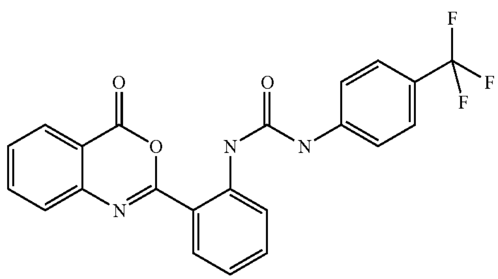 | 381 | 423 | 0.256 | 0.276 | 88 | |
| 30 | 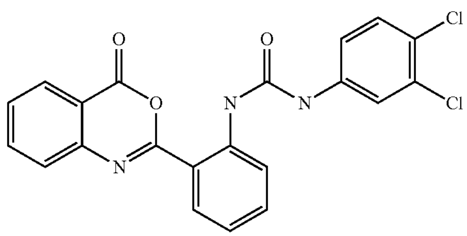 | 380 | 426 | 0.258 | 0.273 | 78 | |

TABLE-continued
| Cmpd. No. | Structure | Excmax [nm] | Flumax [nm] | X | Y | UV brightness [cd/m²] | DTA Peak |
|---|---|---|---|---|---|---|---|
| 31 | 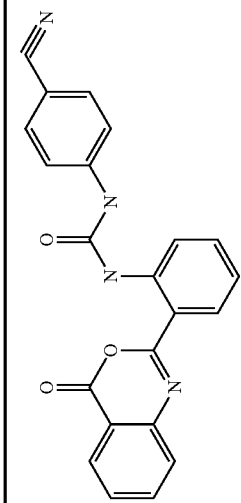 | 0.389 | 426 | 0.225 | 0.223 | 78 | |

Preferred ink compositions of this invention may be prepared by dissolving or dispersing any one or more of these compounds in a suitable solvent such as an alcohol, ester or ketone or the like solvent. For example, about 1 g of 1-phenyl-3-[2-(4-oxo-4H-benzo[d][1,3]oxazin-2-yl)-phenyl]-urea can be dissolved in a solution of 60 g ethanol, 30 g ethyl acetate and 4 g of polyvinyl pyrrolidone resin was added thereto to provide an ink composition that, when printed on a medium and subjected to UV light of about 385 nm, will produce yellow fluorescence at 567 nm. Similar ink compositions may be prepared with the other compounds of this invention. Such ink compositions find especial utility as security inks.

The fluorescent ink compositions of this invention may be used in a multitude of applications and on a great variety of substrates, particularly for security purposes, to provide a wide variety of articles of manufacture. For example, the ink compositions of this invention may be employed on a variety of indicia or data carrier substrates, including but not limited to, uses such as on or in currency, passports, chip cards, checks, check cards, credit cards, debit cards, identity cards, certificates, and bank notes and the like. The invention also includes a process for the preparation of an article of manufacture comprising incorporating the ink composition on or into an article to mark the article and wherein the article is selected from currency, a passport, a chip card, a check, a check card, a credit card, a debit card, an identity card, a certificate, and a bank note. A further aspect of this invention is a process for the preparation of an article of manufacture comprising incorporation a compound of this invention into an article selected from inks for all printing technologies including ink jet and electrophotography technologies, colored or colorless paints, mass coloring polymers, films, coatings, data carriers, security markings, papers, dispersions, spun fibers, dyed fibers, biochemistry tracers and displays. Such use are exemplified, for examples, in WO 98/32799 and WO 03/053980 A1, the disclosures of which are incorporated herein by reference thereto.

While the invention has been described herein with reference to the specific embodiments thereof, it will be appreciated that changes, modification and variations can be made without departing from the spirit and scope of the inventive concept disclosed herein. Accordingly, it is intended to embrace all such changes, modification and variations that fall with the spirit and scope of the appended claims.

What is claimed is:

1. A compound having the general formula (I):

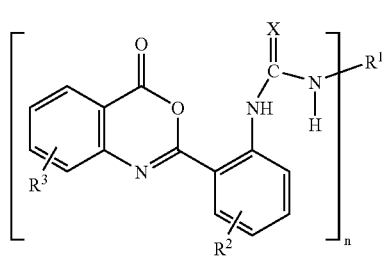

(I)

wherein $R^1$ is a substituted or unsubstituted aryl group, $R^2$ and $R^3$ are each independently selected from the group consisting of an H atom, an alkyl group, an alkoxy group, an alkylcarboxy group and a halogen atom, X is a selected from the group consisting of an oxygen and a sulfur atom, and n is a positive integer of 1 or more.

2. A compound of claim 1 capable of producing fluorescence when subjected to excitation by a suitable ultraviolet source.

3. A compound of claim 2 capable of producing fluorescence within the range of about 560 nm to about 585 nm when subjected to excitation by a suitable ultraviolet source.

4. A compound of claim 2 wherein n is 1.

5. A compound of claim 4 wherein X is oxygen.

6. A compound according to claim 5 wherein the aryl group is an aryl group selected from the group consisting of substituted or unsubstituted phenyl, naphthyl or and a benzoyl group.

7. A compound of claim 6 wherein the aryl group is a substituted aryl group and the substituent is selected from one or more of the groups consisting of an alkyl, alkoxy, alkylcarboxy, alkylcarbonyl, alkyl ester, cyano, halo and haloalkyl group.

8. A compound of claim 7 wherein the alkyl group of the substituent contains from 1 to about 4 carbon atoms.

9. A compound according to claim 7 wherein the substituted aryl group is a substituted phenyl group.

10. A compound according to claim 8 wherein the substituted aryl group is a substituted phenyl group.

11. A compound according to claim 2 wherein n is the integer 2.

12. The compound of claim 2 wherein $R^1$ is phenyl, $R^2$ and $R^3$ are each hydrogen, X is oxygen and n is 1.

13. The compound of claim 2 wherein $R^1$ is para-chloro phenyl, $R^2$ and $R^3$ are each hydrogen, X is oxygen and n is 1.

14. A process for the preparation of a compound of the general formula (I):

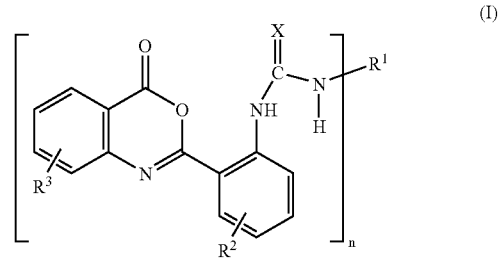

(I)

wherein $R^1$ is a substituted or unsubstituted aryl group, $R^2$ and $R^3$ are each independently selected from the group consisting of an H atom, an alkyl group, an alkoxy group, an alkylcarboxy group and a halogen atom, X is a selected from the group consisting of an oxygen and a sulfur atom, and n is an integer of 1 or 2, comprising reacting a reactant compound of the formula $R^1$—[NCX]$_n$ with a reactant compound selected from the group consisting of anthranoylanthranilic acid and 2-(2-aminophenyl)-4H-3,1-bexzoxazinon under reflux and, in the case of the anthranoylanthranilic acid reactant, dehydrating the reaction product to perform a ring closure, to form a compound of formula (I).

15. A process according to claim 14 wherein in the reactant $R^1$[NCX]$_n$, n is the integer 1, the other reactant is anthranoylanthranilic acid, and the dehydration and ring closure is accomplished with diacetic anhydride as a dehydrating agent.

16. A process according to claim 15 wherein the $R^1$ is a phenyl or substituted phenyl group.

17. A fluorescent ink composition comprising a compound of claim 2.

18. A fluorescent ink composition comprising a compound of claim 3.

19. A fluorescent ink composition comprising a compound of claim 4.

20. A fluorescent ink composition comprising a compound of claim 5.

21. A fluorescent ink composition comprising a compound of claim 6.

22. A fluorescent ink composition comprising a compound of claim 7.

23. A fluorescent ink composition comprising a compound of claim 8.

24. A fluorescent ink composition comprising a compound of claim 9.

25. A fluorescent ink composition comprising a compound of claim 10.

26. A fluorescent ink composition comprising a compound of claim 11.

27. A fluorescent ink composition comprising a compound of claim 12.

28. A fluorescent ink composition comprising a compound of claim 13.

29. An article of manufacture having a fluorescent ink composition of claim 17 on or in the article of manufacture.

30. An article of manufacture of claim 29 wherein the article of manufacture is selected from the group consisting of currency, passports, chip cards, checks, check cards, credit cards, debit cards, identity cards, certificates, and bank notes.

31. A process for the preparation of an article of manufacture comprising incorporating the ink composition of claim 17 on or into an article to mark the article and wherein the article is selected from the group consisting of currency, a passport, a chip card, a check, a check card, a credit card, a debit card, an identity card, a certificate, and a bank note.

32. A process for the preparation of an article of manufacture comprising incorporation a compound of claim 2 into an article selected from the group consisting of an inks, colored or colorless paints, mass coloring polymers, films, coatings, data carriers, security markings, paper, dispersions, spun fibers, dyed fibers, biochemistry tracers and displays.

* * * * *